United States Patent [19]
Gordon et al.

[11] Patent Number: 5,661,774
[45] Date of Patent: Aug. 26, 1997

[54] DUAL ENERGY POWER SUPPLY

[75] Inventors: Bernard M. Gordon, Manchester-by-the-Sea; Hans Weedon, Salem; Iosif Izrailit, Newton, all of Mass.; Timothy R. Fox, Chicago; John F. Moore, Libertyville, both of Ill.

[73] Assignee: Analogic Corporation, Peabody, Mass.

[21] Appl. No.: 671,202

[22] Filed: Jun. 27, 1996

[51] Int. Cl.⁶ ........................................ H05G 1/10
[52] U.S. Cl. ........................ 378/101; 378/105; 378/145
[58] Field of Search ............................. 378/101, 105, 378/106, 108–112, 114, 115, 145, 146, 51, 57

[56] References Cited

U.S. PATENT DOCUMENTS

| | | | |
|---|---|---|---|
| 4,670,893 | 6/1987 | Tsuchiya | 378/112 |
| 4,759,047 | 7/1988 | Donges et al. | 378/57 |
| 4,884,289 | 11/1989 | Glockman et al. | 378/57 |
| 5,132,998 | 7/1992 | Tsutsui et al. | 378/99 |
| 5,182,764 | 1/1993 | Peschmann et al. | 378/57 |
| 5,247,561 | 9/1993 | Kotowski | 378/87 |
| 5,262,946 | 11/1993 | Heuscher | 364/413.18 |
| 5,319,547 | 6/1994 | Krug et al. | 364/409 |
| 5,367,552 | 11/1994 | Peschmann | 378/57 |
| 5,432,339 | 7/1995 | Gordon et al. | 250/231.13 |
| 5,473,657 | 12/1995 | McKenna | 378/4 |
| 5,490,218 | 2/1996 | Krug et al. | 382/100 |

FOREIGN PATENT DOCUMENTS 31 50 306 A1  6/1983  Germany.

OTHER PUBLICATIONS

Alvarez, Robin et al., "Energy–selective Reconstructions in X–ray Computerized Tomography", *Phys. Med. Biol.* 1976, vol. 21, No. 5, 733–744.

*Primary Examiner*—Don Wong
*Attorney, Agent, or Firm*—Lappin & Kusmer LP

[57] ABSTRACT

The disclosed dual energy baggage scanning assembly includes a CT scanning system, and a conveyor belt for transporting items through the CT scanning system, and an improved power supply for the X-ray source of the CT scanner so that a dual energy beam is provided. The power supply alternately powers the X-ray tube of the scanning system at high and low voltage levels at a predetermined rate and comprises at least one high voltage DC power supply for providing a stable, high DC voltage the X-ray tube; means, including at least one waveform generator, for providing a periodic time varying waveform; and coupling means, including a transformer, for coupling the waveform generator to said DC voltage supply so that the total voltage across the cathode and anode of the tube is periodically changed between the high and low voltage levels at the predetermined rate in response to the periodic time varying waveform provided by the waveform generator.

49 Claims, 10 Drawing Sheets

DUAL ENERGY POWER SUPPLY

CROSS-REFERENCE TO RELATED APPLICATIONS

This application is related to U.S. patent application Ser. No. 08/671716, filed Jun. 27, 1996 entitled Quadrature Transverse CT Detection System, assigned to the present assignee, and filed concurrently with the present application (Attorney Docket No. ANA-093), which is hereby incorporated by reference.

1. Field of the Invention

The present invention relates generally to modulated power supplies. More particularly, the invention relates to an improved power supply that is useful in connection with dual energy X-ray systems.

2. Background of the Invention

A common technique of measuring a material's density is to expose the material to X-rays and to measure the amount of radiation absorbed by the material, the absorption being indicative of the density. This well known technique is used in X-ray systems such as CT scanners.

Techniques using dual energy X-ray sources are also known for providing additional information about a material's chemical characteristics, beyond a simple density measurement. Techniques using dual energy X-ray sources involve measuring the X-ray absorption characteristics of a material for two different energy levels of X-rays, and these measurements provide an indication of the material's atomic number in addition to an indication of the material's density. Dual energy X-ray techniques for energy-selective reconstruction of X-ray CT images are described, for example, in Alvarez, Robin et at., "Energy-selective Reconstructions in X-ray Computerized Tomography", *Phys. Med. Biol.* 1976, Vol. 21, No. 5, 733–744; and U.S. Pat. No. 5,132,998.

One proposed use for such dual energy techniques has been in connection with a baggage scanner for detecting the presence of explosives in baggage. As is well known, explosive materials are generally characterized by a relatively high atomic number and are therefore amenable to detection by such dual energy X-ray sources added in machine. A great deal of effort has been made to design a feasible X-ray baggage scanner. Such designs, for example, have been described in U.S. Pat. Nos. 4,759,047 (Donges et at.); 4,884,289 (Glockmann et al.); 5,132,988 (Tsutsui et at.); 5,182,764 (Peschmann et al.); 5,247,561 (Kotowski); 5,319,547 (King et al.); 5,367,552 (Peschmann et al.); 5,490,218 (Krug et al.) and German Offenlegungsschrift DE 31 503 06 A1 (Heimann GmbH).

One prior art type of scanner system using a dual energy X-ray source, which may be referred to as an "alternating beam" type system, is constructed by adding a rotating filter to a third generation type CT scanner. Briefly, third generation type CT scanners include an X-ray source and an array of detectors secured respectively to diametrically opposite sides of an annular shaped disk or platform. The disk is rotatably mounted within a gantry support so that during a scan, the disk continuously rotates about a rotation axis while an X-ray beam generated by the source passes through an object positioned within the opening of the disk to the detector array. Each of the detectors in the detector array generates an output signal representative of the density of a portion of the object being scanned for each measuring interval. The collection of all of the output signals generated by the detector array for any measuring interval is referred to as a "projection", and the angular orientation of the disk (and the corresponding angular orientations of the X-ray source and the detector array) during generation of a projection is referred to as the "projection angle". As the disk rotates around the object being scanned, the scanner generates a plurality of projections at a corresponding plurality of projection angles, and by processing all the data collected at all of the projection angles, the CT scanner generates reconstructed CT images of the object.

Alternating beam type systems include a rotating filter disposed proximal to the X-ray source between the X-ray source and the object being scanned. The rotating filter may be constructed as a rotating circular metal plate, half of the plate being sufficiently thin so as to be relatively transparent to substantially all of the photons generated by the X-ray source, and the other half of the plate being sufficiently thick so as to absorb a relatively large percentage of the lower energy photons and sufficiently thin so as to be substantially transparent to the higher energy photons generated by the X-ray source. The metal plate rotates in the path of the beam generated by the X-ray source so that during half of its rotation cycle the thin portion of the plate is disposed in the beam and substantially all of the photons generated by the X-ray source pass through the plate and are directed towards the object being scanned, and during the other half of its rotation cycle the thicker portion of the plate is disposed in the beam and absorbs some of the lower energy photons so that only the high energy photons and a small percentage of the lower energy photons generated by the X-ray source pass through the plate and are directed towards the object being scanned. So the energy level of the beam incident on the object being scanned alternates with the rotational frequency of the rotating filter: half the time the beam contains relatively few low energy photons, and the other half of the time the beam contains a relatively large amount of low energy photons. By alternating the energy level of the beam in this fashion during a scan, the system measures the X-ray absorption characteristics of the object being scanned for two different energy levels. The metal plate rotates with sufficient frequency so that the CT scanner may generate a plurality of projections for each of the two energy levels during a single 360° rotation of the disk, and the scanner generates two reconstructed CT images for every 360° rotation of the disk, one of the images being generated using data collected in response to the lower energy beam and the other image being generated using the data collected in response to the higher energy beam. A comparison of the two images should theoretically reveal explosive materials of a high atomic number.

In practice, alternating beam type systems are disadvantageous because the two energy levels of the beam are not sufficiently distinct to provide accurate analysis of the atomic number of the object being scanned. Since the beam generated by this type of system contains substantially the same number of high energy photons, regardless of the position of the rotating filter, the different energy levels are not sufficiently distinct.

"Dual detector" type scanner systems represent another known type of scanner system using a dual energy X-ray source. Dual detector type systems are constructed by adding a second detector array to a third generation type CT scanner. In one type of dual detector system, the X-ray source generates two different X-ray beams: a high energy beam and a low energy beam. The system includes a filter for removing most of the low energy photons from one of the two beams and thereby generates the high energy beam. The other, unfiltered beam is the low energy beam. The high energy beam is directed towards one of the detector arrays, and the low energy beam is directed towards the other detector array, so the two detector arrays respectively provide measurements of the absorption characteristics of the object being scanned for two different energy levels. The two detector arrays are different from one another and each must be timed to the specific energy to which it is designed to detect. This type of system shares all the disadvantages of the alternating beam type systems, and is further disadvantageous because the system includes two detector arrays rather than a single array, making the entire detection system complex requiring a very complex data acquisition system to process the data.

In another type of dual detector scanner system, one of the detector arrays is a low energy array configured so as to absorb low energy photons, to be transmissive to high energy photons, and to provide a measurement of the absorption characteristic of the object being scanned for a low energy level. The other detector array is a high energy array and is disposed behind the low energy array so as to intercept the photons passing through the low energy array. Very few low energy photons are incident on the high energy array (since most of the low energy photons are absorbed by the low energy array before they can reach the high energy array). Thus, high energy photons that pass through the object being scanned and through the low energy array are incident on the high energy array. This latter array provides a measurement of the absorption characteristic of the object being scanned for a high energy level. This type of system may also include a filter disposed between the two detector arrays for absorbing even more of the low energy photons which may pass through the fast array, before the beam is intercepted by the high energy detector array. This type of system is disadvantageous because the detector arrays are excessively complex.

Since the energy spectrum of the photons generated by an X-ray source varies as a function of the voltage level applied to the X-ray source, another contemplated method of employing a dual energy X-ray technique is to use a power supply for supplying an alternating voltage level to the X-ray source of a CT scanner so that the X-ray source periodically changes between the two different energy levels. Such a power supply would preferably generate an output signal characterized by a periodically changing voltage that changes rapidly between two high voltage levels (e.g., −160 kV (kilovolts) and −100 kV) to permit generation of X-ray beams having sufficiently distinct energy levels. Ideally, the power supply would periodically change between the two high voltage levels with sufficient frequency to permit generation of a plurality of projections at each of the two energy levels during a single 360° rotation of the disk. However, prior art high voltage power supplies currently used to provide a high voltage DC signal to the X-ray tubes of the type used in CT scanners cannot be easily modified to provide the periodically changing voltage at the change rate required to power the X-ray source so that the latter provides a dual energy X-ray beam. The reason suitable periodic change rates in the voltage would be difficult to accomplish is that high voltage DC power supplies typically use unidirectional rectifiers as a voltage multiplier together with filter capacitors, the latter having poor time responses, i.e., sudden increases in voltage will charge the capacitors, but the capacitors do not necessarily discharge quickly when the voltage suddenly drops. Thus, the rate of decay has primarily been limited by capacitance and is typically too slow with regard to the desired switching rate of a baggage scanner for example. Also, since pulling the voltage down from one high voltage to another would require dissipating large amounts of energy, such a power supply would consume excessively large amounts of power.

OBJECTS OF THE INVENTION

It is an object of the present invention to substantially reduce or overcome the above-identified problems of the prior art.

Another object of the present invention is to provide an improved power supply for generating a periodic changing high voltage signal that changes between two high voltage levels at a relatively high changing rate and is particularly useful in driving an x-ray source at two different intensity levels at the changing rate.

Yet another object of the invention is to provide an improved high voltage power supply for use with a CT scanner for generating a dual energy X-ray beam.

Still another object of the present invention is to provide an improved baggage scanner including a CT scanning system having a high voltage power supply for generating and applying a periodically changing high voltage to the X-ray source of the system so that the source provides a dual energy X-ray beam.

And yet another object of the present invention is to provide a high voltage power supply for supplying power to an x-ray tube so as to generate a dual energy X-ray beam, the power supply including at least one DC power supply having unidirectional rectifiers and storage capacitors.

And still another object is to provide relatively stable, modulated high DC voltage signals between the anode and cathode of an x-ray source of a CT scanner for switching the output beam of the X-ray source between a high and low energy level output.

And yet another object of the present invention is to provide a dual energy baggage scanner including components for generating an X-ray beam that periodically changes between a high energy level and a low energy level at the desired rate suitable for a baggage scanner.

And still another object of the present invention is to provide the combination of an improved power supply for providing a periodically changing voltage at a suitable modulation rate to an X-ray source so as to generate a dual energy X-ray beam so that an improved dual energy scanner can be provided.

And yet another object of the present invention is to provide a high voltage power supply for providing a high voltage output which varies between two high voltage levels at a periodically varying, relatively fast rate with little or no power loss.

And still another object of the present invention is to provide a baggage scanner including components for synchronizing the period of the dual energy X-ray beam with rotation of a rotating platform such as a rotating gantry disk.

And yet another object of the present invention is to provide a scanner including components for transporting items such as baggage through the CT scanner.

SUMMARY OF THE INVENTION

These and other objects of the present invention are achieved by an improved power supply for use in powering an X-ray source of the type producing a dual energy X-ray beam and that may be used, for example, in a baggage scanner. The power supply includes at least one high voltage DC power supply for providing a stable, high DC voltage; means, including a waveform generator, for providing a periodic time varying waveform; and coupling means, including at least one transformer, for coupling the waveform generator to the high voltage DC power supply so as to provide a modulated voltage at the desired modulation rate which when applied to the X-ray source will cause the latter to generate a dual energy X-ray beam between the desired high and low levels at a predetermined rate.

The transformer preferably provides DC isolation between the output of the waveform generator and the output of the high voltage DC voltage power supply. The transformer is preferably a step up transformer so that the waveform generator can provide a relatively low voltage output. The step up transformer has a relatively fast time response so that the periodically changing voltage can be easily changed in both directions at the predetermined rate. The use of the transformer results in very little power loss with each cycle of the generated waveform, such losses generally being substantially limited to transformer losses.

In accordance with another aspect of the present invention, the power supply may be used to supply power to an X-ray source in a CT scanner so as to provide an improved baggage scanner.

According to another aspect, the CT scanner may include components for synchronizing the rotation of a rotating gantry disk with the periodic rate of change of the waveform produced by the waveform generator.

And yet another aspect of the present invention is to utilize a rotating filter in the X-ray beam provided by the X-ray source synchronized with the modulation rate of the power supply so as to enhance the differences between the high and low energy beams passing through the scanned objects.

According to yet another aspect, the modulation power supply and CT scanner may be used in a baggage scanning assembly that includes a conveyor belt for transporting items of baggage through the CT scanner.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein.

DETAILED DESCRIPTION OF THE DRAWINGS

Figure 1:
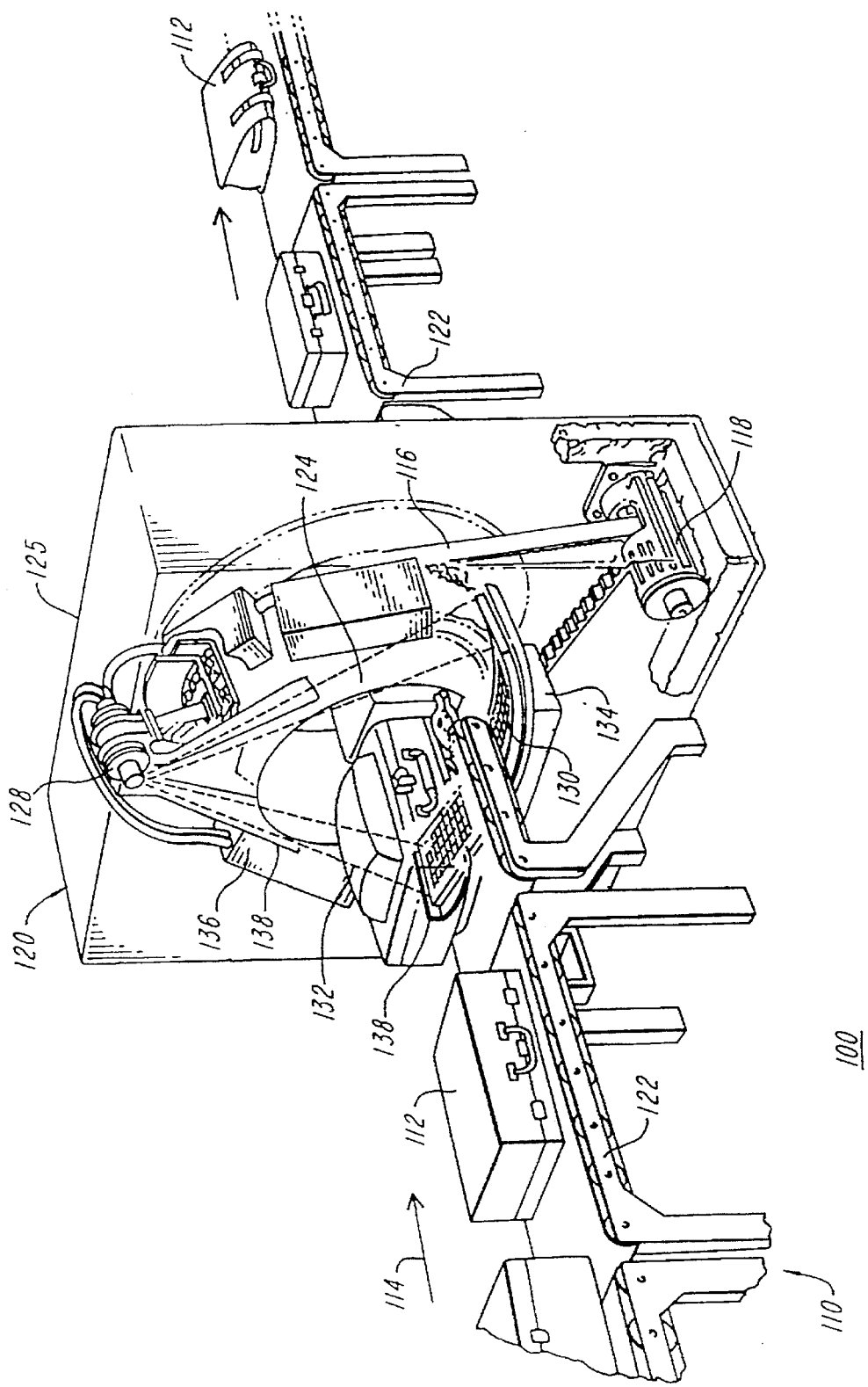
FIG. 1 shows a perspective view of a dual energy baggage scanning assembly constructed according to the invention.
Figure 2:
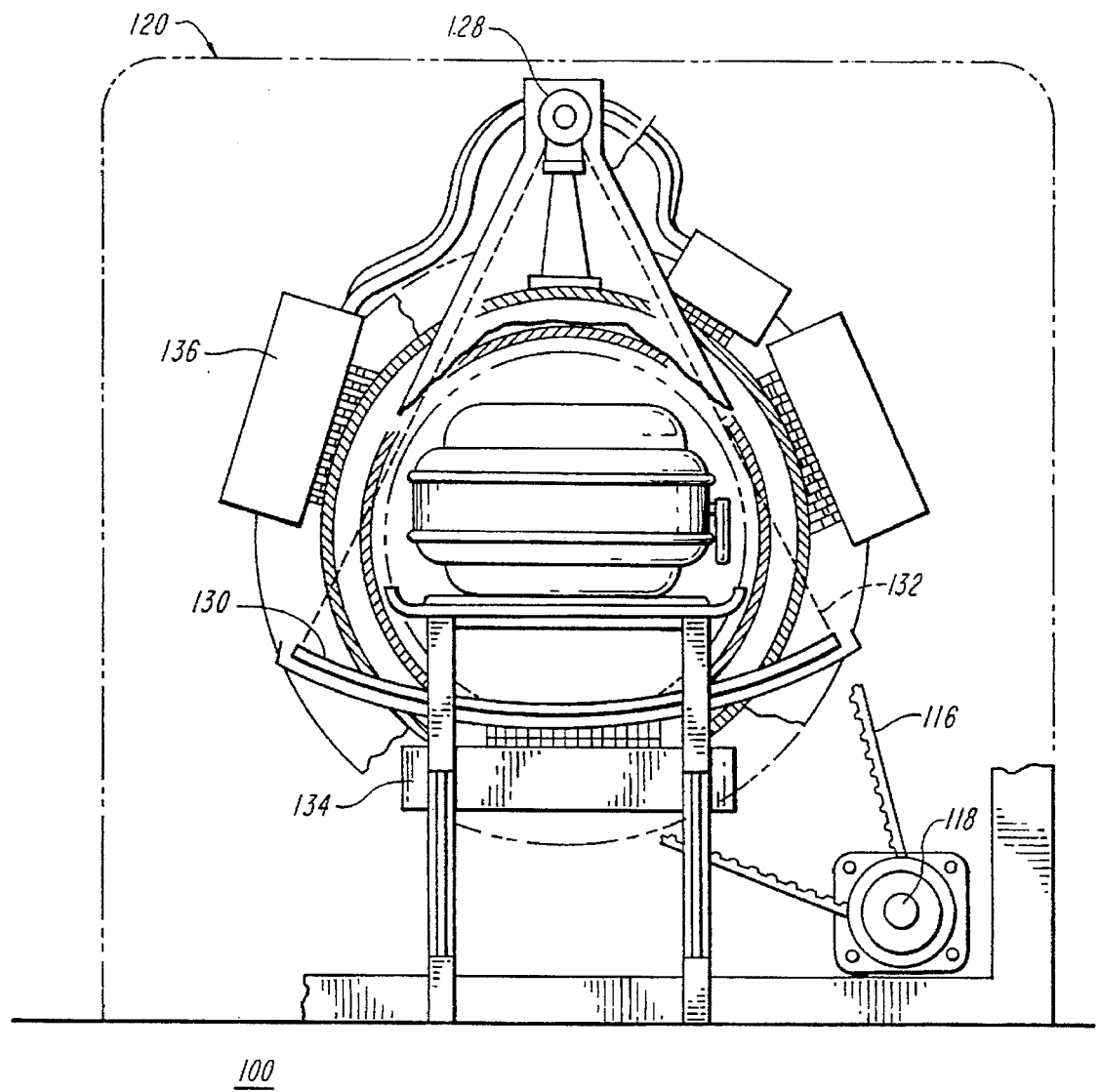
FIG. 2 shows a cross sectional end view of the assembly shown in FIG. 1.
Figure 3:
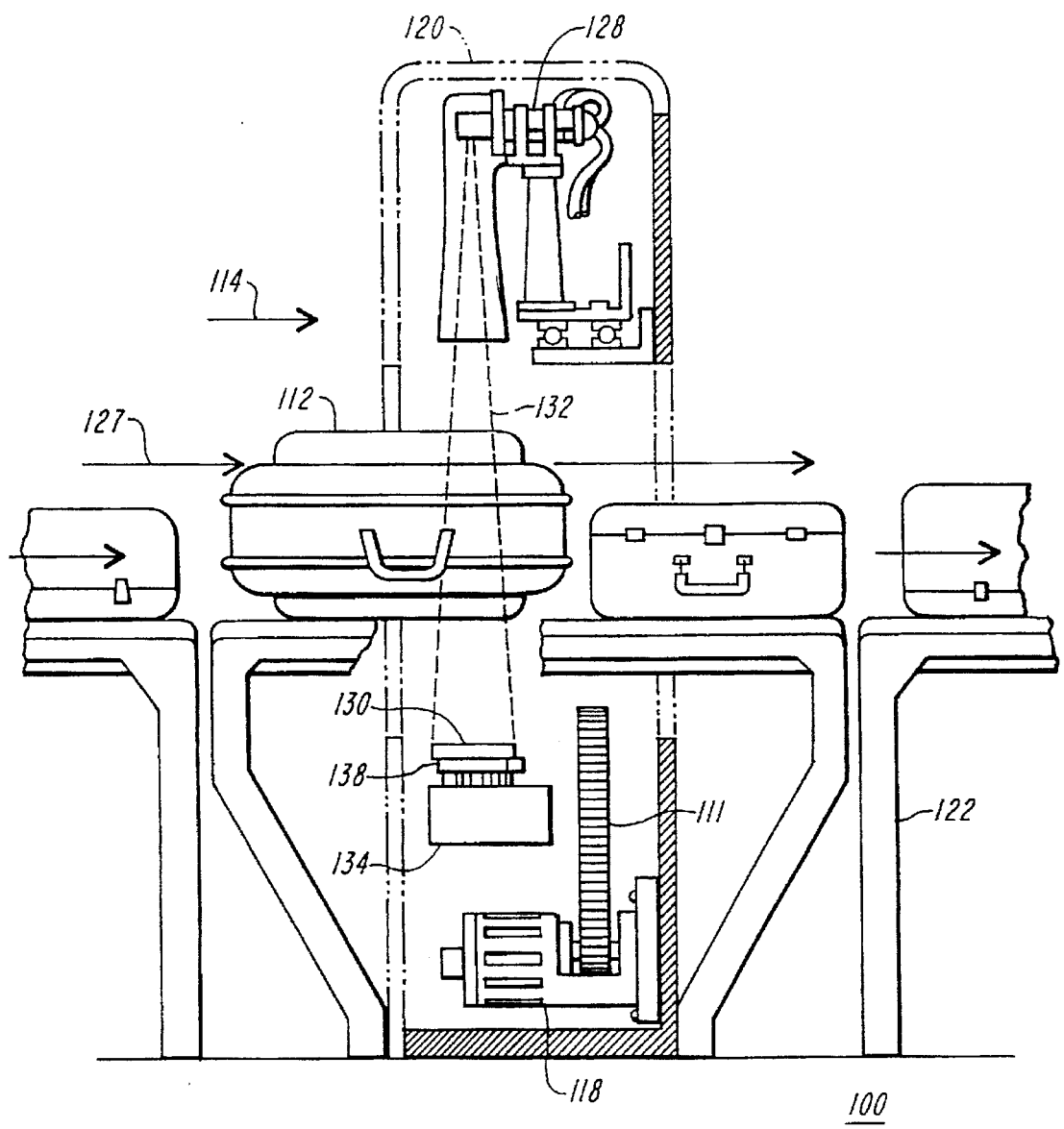
FIG. 3 shows a cross sectional radial view of the assembly shown in FIG. 1.

FIGS. 1–3 shows a scanning assembly 100 constructed according to the invention, and designed for scanning baggage in order to detect explosive materials. Assembly 100 includes a conveyor System 110 for conveying baggage, or luggage, 112 in a direction indicated by arrow 114 through a central aperture of a CT scanning system 120. Conveyor system 110 is illustrated as including a plurality of individual conveyor sections 122, however, other forms of conveyor systems may of course be used. The conveyor system includes motor driven belts for supporting the luggage. CT scanning system 120 includes an annular shaped rotating platform, or disk, 124 disposed within a gantry support 125 for rotation about a rotation axis 127 (shown in FIG. 3) that is preferably parallel to the direction of travel of the baggage 112, such direction of travel being indicated by arrow 114. Disk 124 is driven about rotation axis 127 by any suitable drive mechanism, such as a belt 116 and motor drive system 118, or other suitable drive mechanism, such as the one shown in U.S. Pat. No. 5,473,657 issued Dec. 5, 1995 to Gilbert McKenna, entitled X-ray Tomographic Scanning System, and assigned to the present assignee. Rotating disk 124 defines a central aperture 126 through which conveyor system 110 transports the baggage 112. System 120 includes an X-ray robe 128 and an array of detectors 130 which are disposed on diametrically opposite sides of the disk 124. Detectors 130 are preferably arranged as a two-dimension array of the type described more fully in the above-referenced U.S. patent application Ser. No. 08/671716, filed Jun. 27, 1996, although other detector arrangements can be used depending on the design criteria of the system and its particular intended use. System 120 further includes a data acquisition system 134 (shown in FIGS. 2 and 3) for receiving and processing signals generated by detector array 130, and an X-ray tube control system 136 (shown in FIG. 1 and 2) for supplying power to, and otherwise controlling the operation of, X-ray tube 128 so as to provide a dual energy X-ray source. System 120 also includes suitable shielding, such as shields 138, which may be fabricated from lead, for preventing radiation from propagating beyond gantry 125.

In operation, X-ray tube 128 preferably generates a cortically or fan shaped beam 132 of X-rays of predetermined geometry (as best seen in FIG. 3) that passes through an imaging field, through which baggage 112 is transported by conveying system 110. Beam 132 is intercepted by detector array 130, which in turn generates signals representative of the densities of the portions of baggage 112 passing through the beam. Disk 124 rotates about its rotation axis 127 thereby transporting X-ray source 128 and detector array 130 in circular arcs about baggage 112 as the baggage is continuously linearly transported through central aperture 126 by conveyor system 110 so as to generate a plurality of projections at a corresponding plurality of projection angles. Scanning system 120 uses known helical volumetric reconstruction techniques to generate volumetric CT images representative of the baggage 112 passing through the beam.

As described in greater detail hereinafter, control system 136 generates an output signal that is characterized by a voltage that periodically changes between a first high voltage level $V_1$ (e.g., −160 kV) and a second high voltage level $V_2$ (e.g., −100 kV) at a relatively high modulation or change rate $f_1$ (for example, between 200 and 800 Hz). This output signal is applied to X-ray tube 128. The latter generates beam 132 as a relatively high energy beam in response to the first high voltage level $V_1$, and a relatively low energy beam in response to the second high voltage level $V_2$, so that beam 132 alternates between two energy levels at the switching frequency $f_1$ as disk 124 rotates about the baggage 112. The projections generated by detector array 130 in response to the high energy beam may be referred to as "high energy projections", and similarly the projections generated by detector array 130 in response to the low energy beam may be referred to as "low energy projections". Since the energy level of beam 132 alternates with the high frequency of $f_1$, CT scanning system 120 generates a plurality of high energy projections and a plurality of low energy projections for each 360° rotation of disk 124.

Data acquisition system 134 receives all the high energy and low energy projections generated by detector array 130 and generates therefrom, in cooperation with other processors or computers (not shown), reconstructed CT volumetric representations of baggage 112. For every 360° rotation of disk 124, CT scanning system 120 generates two CT volumetric representations of baggage 112, one of the volumetric representations being generated in response to the high energy projections, and the other volumetric representation being generated in response to the low energy projections. Other processing components or computers (not shown) then analyze the two volumetric representations to determine whether the scanned baggage contains explosive material. Bags suspected of containing explosive material may be automatically removed from conveyor system 110, and, if desirable automatically transported to another location (not shown) for further examination. Alternatively, the information can be suitably displayed on an accompanying monitor (not shown), and/or a suitable alarm can be provided.

Preferably, the energy level of beam 132 alternates at a modulation rate of $f_1$ that is much larger than the rotation rate of speed of the disk 124 so that CT scanning system 120 generates two volumetric representations for a single 360° rotation of the disk. Alternatively, system 120 can generate the beam 132 so that its energy level alternates with a much lower frequency, e.g., with a frequency that is equal to the rotational frequency of disk 124, for example, so that tube 128 generates a low energy beam for an entire 360° rotation of platform 124 and then generates a high energy beam for the next 360° rotation of platform 124. However, in this latter embodiment disk 124 rotates about baggage 112 twice to generate two CT volumetric representations of the baggage in response to two distinct energy levels, and the baggage 112 is correspondingly transported through system 120 relatively slowly. However, since the speed at which bags can be scanned is an important design criteria for a baggage scanner, the rate $f_1$ with which the energy level of the beam 132 alternates is preferably significantly higher than the rotational frequency of disk 124 so that the baggage 112 may be continuously and rapidly transported through scanning system 120 while system 120 generates two distinct CT volumetric representations of the baggage for every 360° rotation of platform 124.

In one preferred embodiment, the disk 124 rotates 360° every two thirds of a second, the dimension of the detector array 130 is 15.5 cm in the Z-direction (a direction parallel to rotation axis 127), the linear velocity of baggage 112 (as transported by conveyor system 110) is substantially equal to about 0.131 meters per second, and the rate $f_1$ is equal to 533 Hz, although those skilled in the art will appreciate that there is a relatively large degree of flexibility in the choice of these dimensions and rates. For these dimensions and rates, assembly 100 can scan approximately 675 items of baggage per hour. In another embodiment, the disk 124 rotates 360° every two thirds of a second, the dimension of the detector array is 23.256 cm in the Z-direction, the linear velocity of baggage 112 is substantially equal to 0.175 meters per second, and $f_1$ is equal to 800 Hz, and in this embodiment, assembly 10 can scan approximately 900 items of baggage per hour.

In accordance with the present invention the X-ray tube control system 136 for controlling the X-ray tube 128 as a dual energy source of X-rays preferably includes at least one high voltage DC power supply for providing a stable, high DC voltage between the cathode and anode of the X-ray tube; and at least one transformer circuit for coupling the output of a waveform generator to the output of the DC power supply so that the total voltage across the cathode and anode is modulated between the desired high and low voltage levels at the predetermined rate as a function of the output of the waveform generator.

While the present invention relates to the voltage applied between the cathode and the anode of an X-ray tube, the benefits of dual-energy X-ray operations are recognized by understanding that the X-ray beam contains a spectrum of photons of substantially all energies up to that corresponding to the applied voltage. The purpose of the invention is to create two values of the "effective voltage" in the X-ray beam. This "effective voltage" can be thought of as a kind of average over all of the photons in the beam, but it is not a true mathematical average. This is because the shape of the spectrum detected in an X-ray system is a function of many factors other than the applied voltage. These include the "heel angle" (the tilt in the face of the anode), the "inherent filtration" represented by the exit window through which the X-ray beam passes out of the tube, the thickness and the nature of the attenuating body, which is to be examined by the X-rays, and the energy dependent spectrum of sensitivity of the X-ray detector. In general, the effective energy is substantially lower than the applied voltage, ranging from about 40% to about 70% of the latter, depending upon the aforementioned factors. Accordingly, when the energy of a beam is referred to herein, it should be understood to mean the effective energy of the spectrum of individual photons.

Figure 4:
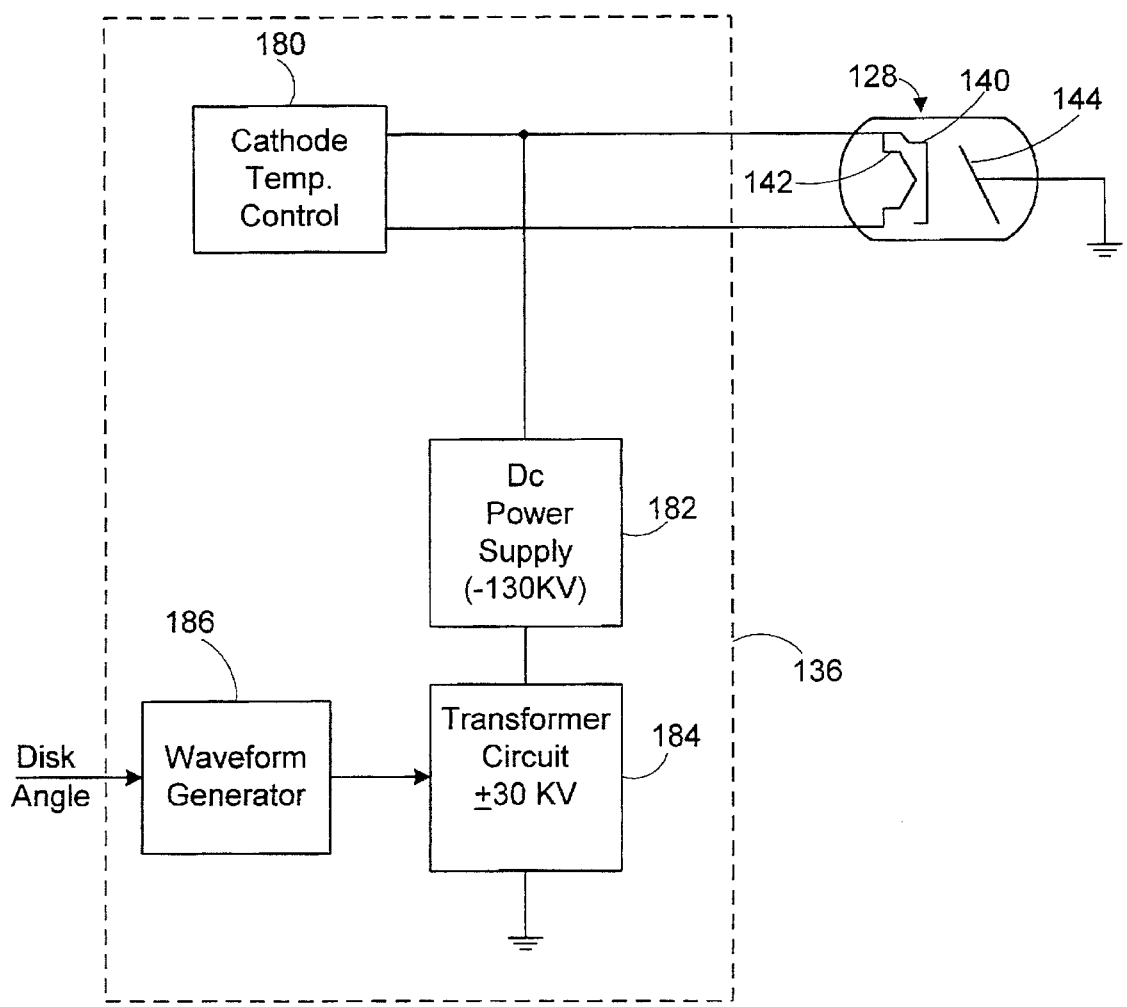
FIG. 4 shows a block diagram of one preferred embodiment of the power supply and X-ray tube of the assembly shown in FIG. 1, designed according to the present invention.

FIG. 4 shows a block diagram of one preferred embodiment of the control system 136 for controlling the X-ray tube 128. In the illustrated embodiment of FIG. 4, X-ray tube 128 is of the hot cathode type and includes a cathode 140, a filament 142 for heating the cathode 140, and a water cooled, grounded anode 144. As is well known, in such tubes the energy spectrum of the X-ray beam generated by tube 128 is a function of the voltage applied to the cathode 140 relative to the anode, whereas the X-ray flux generated by the tube is a function of the electron current flowing from cathode 140 to anode 144 which is in turn a function of the temperature of cathode 140. As shown in FIG. 4 a cathode temperature control system 180 is provided for controlling the temperature of the filament 142 of the cathode 140 of X-ray tube 128. In this embodiment one high voltage, DC power supply 182 is connected to the cathode, so that a stable high DC voltage is applied to the cathode of the tube from one source. In addition, the transformer circuit 184 preferably is connected between the DC power supply 182 and system ground. A waveform generator 186, provides the signal representative of the modulation rate $f_1$, to the transformer circuit 184 to which the circuit responds so that the stable DC output signal of power supply 182 is modulated or periodically varies at the rate $f_1$. The transformer circuit 184 therefore functions to couple the output of the waveform generator 186 to the output of the DC power supply so that a modulating signal provided as a function of the output of the waveform generator can be used to modulate the output of the DC power supply. The waveform generator 186 preferably generates a waveform which periodically varies as a function of $f_1$, which in turn is a function of the angular position of a rotating element, as described in detail hereinafter.

Figure 5:
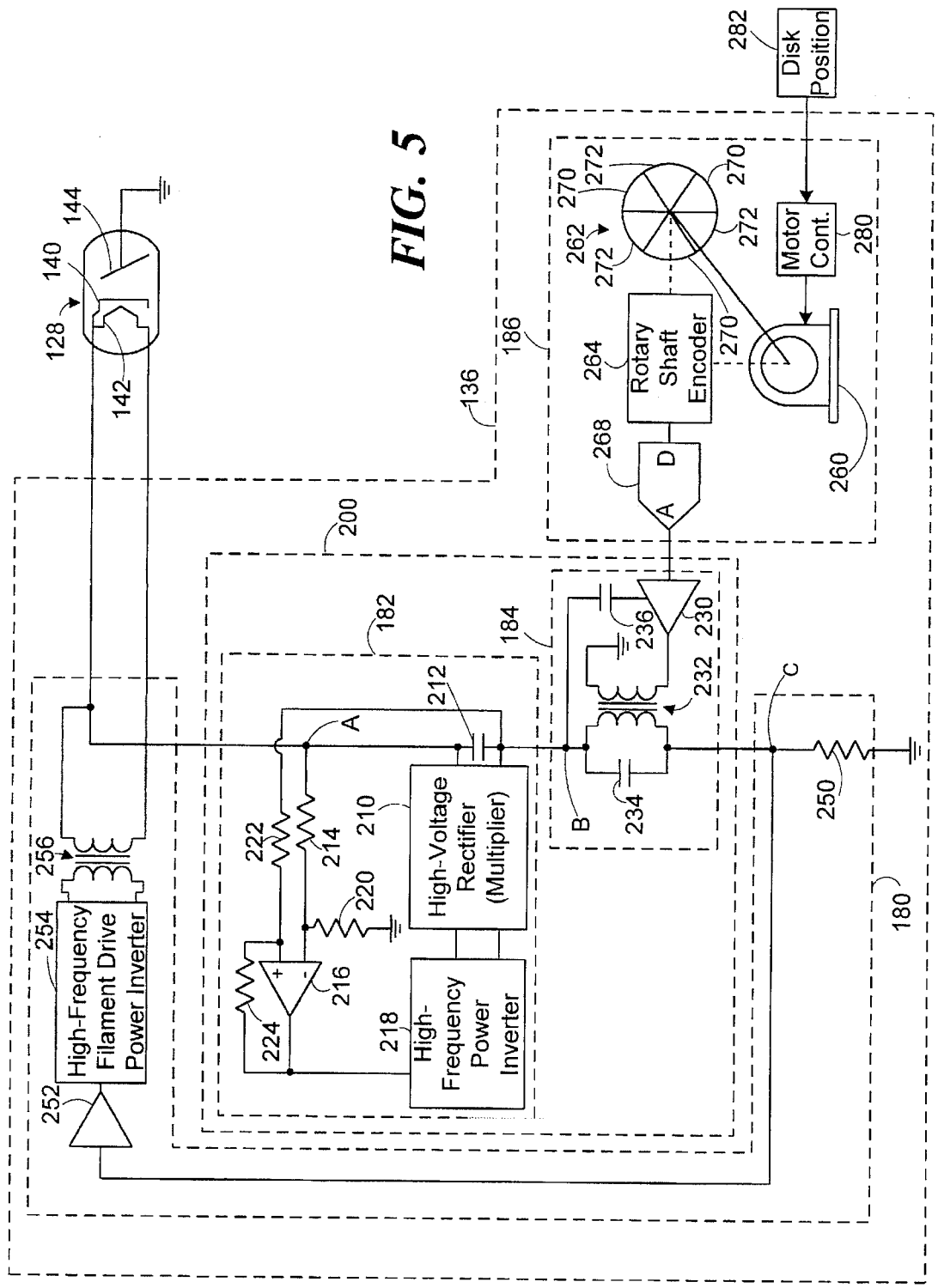
FIG. 5 shows a partial block and partial schematic diagram of a detailed illustration of the FIG. 4 embodiment.

A preferred implementation of FIG. 4 is shown in FIG. 5. As shown, control system 136 includes a cathode temperature control system 180 and a high voltage power supply 200, comprising the high DC voltage supply 182 and the transformer circuit 184. The power supply may also be considered to include the waveform generator 186 although as shown the waveform generator is shown as separate from power supply 200. As will be discussed in greater detail below, power supply 200 generates a high voltage signal that is modulated at the relatively high rate $f_1$ between the first high voltage level $V_1$ and the second high voltage level $V_2$, and applies this high voltage modulated signal to the cathode 140 of X-ray tube 128 relative to anode 144. Since tube 128 generates a high energy beam in response to the first voltage level $V_1$, and a low energy beam in response to the second voltage level $V_2$, power supply 200 controls the energy spectrum of the beam by alternating the voltage applied to tube 128. Waveform generator 186 controls the switching frequency $f_1$ of the high voltage signal generated by power supply 200, and thereby controls the frequency at which the tube 128 generates the high and low energy beams. Cathode temperature control system 180 controls the temperature of the cathode 140 in X-ray tube 128 by controlling the current flowing through heating filament 142 and thereby controls the X-ray flux generated by tube 128.

Describing FIG. 5 in more detail, cathode temperature control system 180 includes current sense resistor 250, an amplifier 252, a high frequency power inverter 254, and a transformer 256. Resistor 250 is electrically connected between the modulating circuit 184 (at node C) and system ground. The voltage across resistor 250 representative of the sensed current through the resistor is applied to the input of amplifier 252. This voltage is relatively small compared to the voltage applied between the cathode and anode, and therefore has an inconsequential effect on the voltage levels used to generate the low energy and high energy beams. The amplifier 252 generates an output signal that is applied to power inverter 254 which in turn generates an output signal that is applied to the primary of transformer 256. The secondary of transformer 256 is coupled in parallel with filament 142 of X-ray tube 128, and one end of the secondary is electrically connected to node A.

In operation, the voltage across current sense resistor 250 is representative of the electron current flowing from cathode 140 to anode 144 (since the current flowing through resistor 250 is equal to the current flowing into cathode 140), and this voltage is applied to amplifier 252. The latter generates an output signal representative of the voltage across resistor 250 and applies this signal to high frequency power inverter 254 which generates therefrom an AC signal, the amplitude of which is representative of the voltage across resistor 250. This AC signal is applied to the primary winding of transformer 256 and the secondary winding of transformer 256 generates therefrom the AC signal that is applied to filament 142.

Cathode temperature control system 180 controls the temperature of cathode 140 according to a function of the electron current flowing from cathode 140 to anode 144. The gain of amplifier 252 is preferably selected so as to increase the temperature of cathode 140 in response to decreases in the voltage across resistor 250, and to decrease the temperature of cathode 140 in response to increases in the voltage across resistor 250 and thereby maintains the average value of the temperature of cathode 140 at a substantially constant temperature.

The high voltage DC power supply 182 as shown in FIG. 5 includes a capacitor 212 connected between the cathode 140 of the tube 128 and the transformer circuit 184. A stable, high DC output voltage $V_3$ is provided across the capacitor 212 and thus to the cathode of the tube 128. In the preferred implementation of FIG. 5, this high DC voltage $V_3$ is equal to −130 kV. The DC voltage source 182 also includes a high-voltage rectifier 210 functioning as a voltage multiplier for providing the DC voltage across capacitor 212, a high frequency power inverter 218 having its output connected to the input of the rectifier 210, and a voltage stabilizing amplifier 216, connected in a feedback arrangement for sensing the voltage across capacitor 212 and providing a feedback signal to the inverter 218. The stabilizing amplifier 216 is preferably a differential amplifier having its inverting input connected (1) through resistor 214 to the node A between the cathode 142 of tube 128 and capacitor 212, and (2) through resistor 220 to system ground. The non-inverting input of amplifier 216 is connected through resistor 222 to the node B between the capacitor 212 and the transformer circuit 184. These components essentially form a high voltage DC power supply which generate a stable, high voltage DC signal characterized by an intermediate high voltage level $V_3$ (e.g., −130 kV) across capacitor 212. This DC power supply 182 is similar to the DC supply used in the Anatom 2000, a CT scanner that is manufactured by the assignee of the present invention.

In operation, rectifier 210 generates a high voltage across capacitor 212, and resistors 214, 220, 222, 224, amplifier 216, and power inverter 218 form a control loop for stabilizing the high voltage generated by rectifier 210 so as to maintain the voltage across capacitor 212 equal to the intermediate voltage level $V_3$. Amplifier 216 provides a low voltage output signal representative and as a function of the output voltage of the rectifier 210 applied across capacitor 212. The amplifier 216 applies this signal to power inverter 218, which in turn generates a high frequency oscillating signal that is applied to rectifier 210. Thus, resistors 214, 220, 222, 224, amplifier 216, and power inverter 218 cooperate to sense the voltage level across capacitor 212 and to adjust the amplitude of the signal applied to rectifier 210 by power inverter 218 so as to maintain and therefore stabilize the voltage level across capacitor 212 equal to the intermediate voltage level $V_3$.

The transformer circuit 184 of the power supply 200 includes a low voltage power amplifier 230, a transformer 232, a capacitor 234, and a feedback capacitor 236, and these components form a high voltage, AC power supply, that is coupled between the capacitor 212 of the DC power supply 182 and resistor 250 of the cathode temperature control system 180, for establishing an AC voltage between nodes B and C that preferably periodically varies between a positive voltage level $+V_{AC}$ (e.g., +30 kV) and a negative voltage level $-V_{AC}$ (e.g., -30 kV). More specifically, the output of amplifier 230 is preferably connected to one end of the primary winding of transformer 232, the other end being connected to system ground. The secondary winding of transformer 232 is connected to opposite ends of the capacitor 234. It should be appreciated that the transformer can be used to multiply the voltage output of amplifier 230, thus allowing the amplifier 230 to be a low voltage AC power amplifier, which is easier to design and implement than a high voltage AC amplifier. For example, the power amplifier 230 can be designed to provide an AC voltage varying between +1 kV to -1 kV. The ratio of turns of the secondary winding to the primary winding can be 30:1 so that the voltage generated between nodes B and C varies between the required +30 kV and -30 kV.

The input to the amplifier 230 is provided by the waveform generator 186. The latter provides a time varying periodic pulse or signal which preferably represents the position of the disk 124 and changes at a rate $f_1$, so that the frequency $f_1$ is synchronous with the rotation of disk 124, as described in greater detail hereinafter.

Thus, in operation, the time varying periodic input signal generated by waveform generator 186 and applied to power amplifier 230 is a relatively low voltage signal that is characterized by the switching frequency of $f_1$. In response to this signal, amplifier 230 generates a low voltage AC signal characterized by the same periodic rate of change $f_1$, and applies this signal to the primary of transformer 232. Transformer 232 steps up the voltage of the signal applied to its primary so that the secondary of transformer 232 generates a high voltage AC signal that is also characterized by the periodic rate of change $f_1$. Feedback capacitor 236 effectively blocks DC components and generates a low voltage AC signal representative of the AC voltage level at node B, and applies this low voltage AC signal to the control terminal of power amplifier 230. Power amplifier 230 adjusts its gain as a function of the signal applied to its control terminal so as to stabilize the level of the AC voltage provided across capacitor 234 at $\pm V_{AC}$.

Capacitor 234 is preferably selected to operate with the inductance provided by the secondary winding of transformer 232 so that capacitor 234 and the secondary of transformer 232 form a resonant LC circuit that resonates at frequency $f_1$. As will be discussed in greater detail below, in preferred embodiments of power supply 200 the rate $f_1$ has a relatively small allowable range of variation, and using capacitor 234 to form a resonant circuit with the secondary winding of transformer 232 improves the efficiency of power supply 200. In some embodiments of power supply 200 it may be desirable that capacitor 234 is a variable capacitor so that the capacitor can be adjusted in order to select the desired frequency $f_1$.

Figure 6:
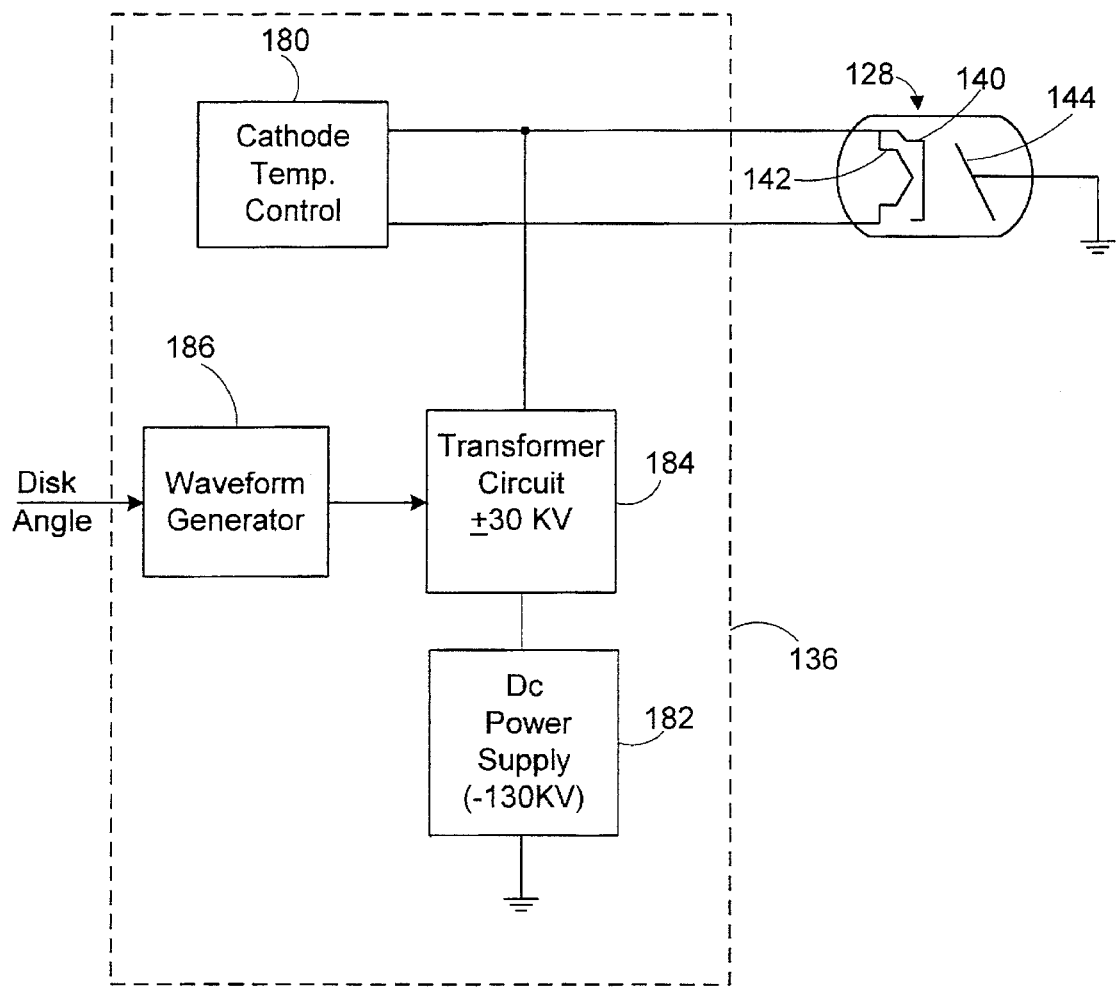
FIG. 6 shows a block diagram of a second preferred embodiment of the power supply and X-ray tube of the assembly shown in FIG. 1, designed according to the present invention.
Figure 7:
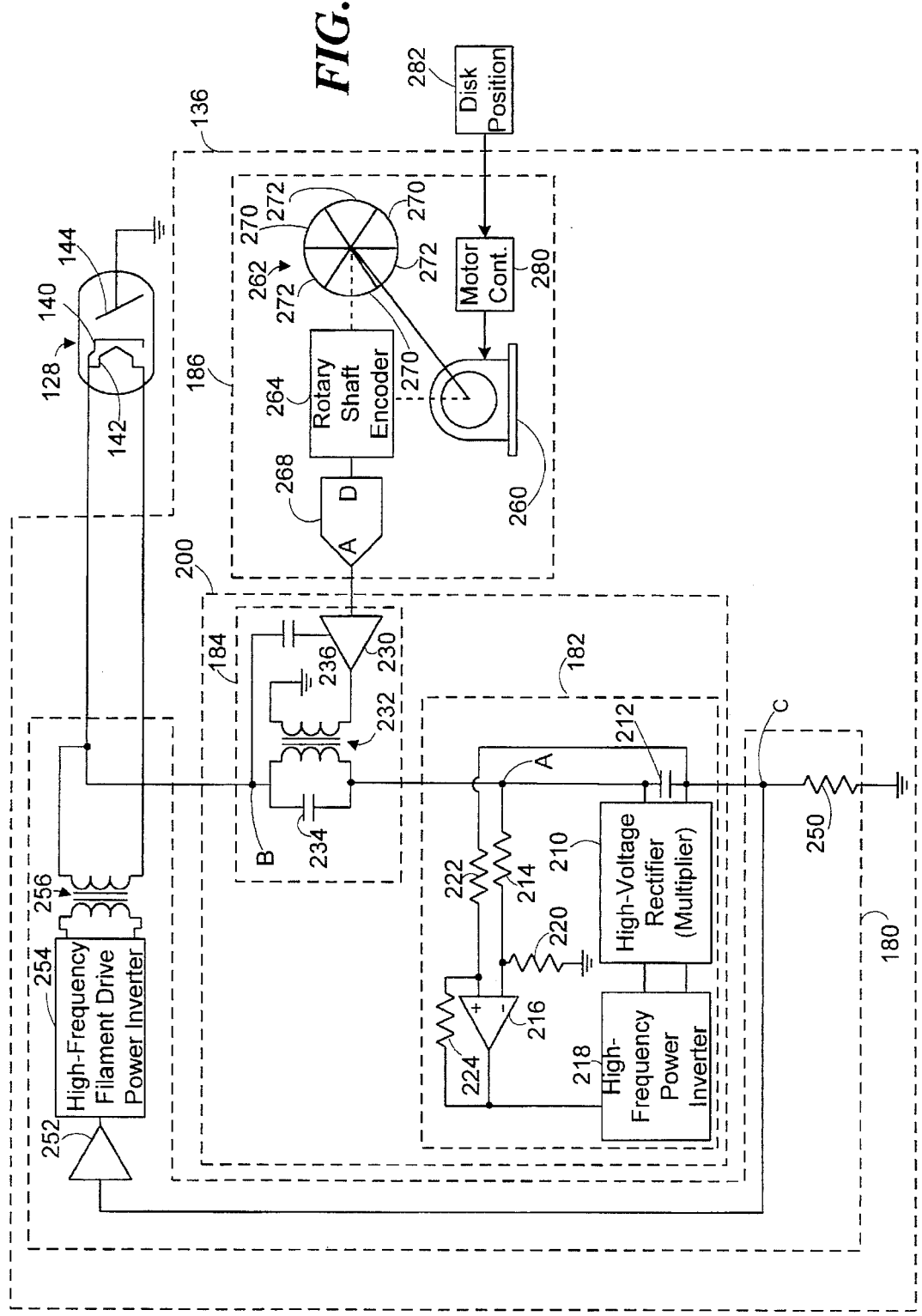
FIG. 7 shows a partial block and partial schematic diagram of a detailed illustration of the FIG. 6 embodiment.

Feedback capacitor 236 may be a single capacitor as shown, or it may be implemented in any one of several other ways. For example, capacitor 236 can be implemented as a voltage divider formed by two series capacitors: a first capacitor which is a high voltage capacitor (i.e., a capacitor that is insulated for high voltages) and a second capacitor which is a low voltage capacitor, the first capacitor being coupled between node B and the second capacitor, and the second capacitor being coupled between the first capacitor and the control terminal of power amplifier 230. In alternative embodiments, it may also be desirable to include a second feedback capacitor (not shown) coupled between node C and an additional control terminal (not shown) of amplifier 230 so that amplifier 230 receives feedback from both nodes B and C. This preferred arrangement is shown in block diagram in FIG. 6. FIG. 7 shows a partial block and partial schematic diagram of a detailed illustration of the FIG. 6 embodiment.

Since rectifier 210 generates an intermediate DC voltage level $V_3$ across capacitor 212, and since transformer 232 generates an AC signal varying between $+V_{AC}$ and $-V_{AC}$ between nodes B and C, power supply 200 generates a modulated signal between nodes A and C that is characterized by a voltage that is modulated at the rate $f_1$ between $V_1$ and $V_2$, where $V_1$ equals $V_3$ minus $V_{AC}$ (e.g., -160 kV=-30 kV -30 kV), and where $V_2$ equals $V_3$ plus $V_{AC}$ (e.g., -100 kV=-130 kV+30 kV).

Those skilled in the art will appreciate that in alternative embodiments of system 136, the relative positions of DC power supply 182 and transformer circuit 184 may be reversed so that transformer circuit 184 is connected between cathode 140 and DC supply 182, and DC supply 182 is connected between transformer circuit 184 and resistor 250 of temperature control system 180.

Use of transformer 232 simplifies the implementation of the AC portion of power supply 200 since only transformer 232 and capacitors 234, 236 are insulated for high voltages. All other components used to generate the AC voltage, such as amplifier 230 and frequency control system 204 are referenced to system ground and operate at low voltages. If transformer 232 were eliminated and control system 136 was designed to include a conventional switching type power supply, all components in the AC portion of supply 200 would necessarily be expensive high voltage components referenced at the intermediate voltage level $V_3$ rather than ground. Use of transformer 232 also advantageously allows power supply 200 to generate a voltage that modulates between $V_1$ and $V_2$ while consuming a relatively small amount of power. If a supply for supplying such a modulated voltage were constructed using unidirectional rectifiers, such a supply would necessarily have to dissipate large amounts of energy every time the supply pulled the voltage down from the high voltage $V_1$ to the lower voltage $V_2$. Since the average power transferred through transformer 232 is zero (excluding the relatively low transformer losses), supply 200 generates the modulated voltage in an efficient manner and does not consume excessive energy.

Node A is electrically connected to the cathode 140 of X-ray tube 128 and the high voltage signal at node A causes an electron current to flow from cathode 140 towards the anode 144 and the electrons impacting on the surface of anode 144 causes generation of X-rays. As stated above, X-ray tube 128 generates a relatively high energy X-ray beam in response to $V_1$ and generates a relatively low energy X-ray beam in response to $V_2$. Power supply 200 thus cooperates with X-ray tube 128 to generate a dual energy X-ray beam that periodically varies between two energy levels at the rate $f_1$.

The AC signal generated by waveform generator 186 and applied to amplifier 230 can be any type of periodic time varying signal, such as a pulse train in the form, for example, of a square or trapezoidal waveform, or a continuously varying signal, such as a sinusoidal signal. Ideally, the AC signal is a square waveform, and the transformer circuit 184 and waveform generator 186 are designed for a square waveform. In addition, the AC signal is preferably a symmetrical waveform, i.e., provides an average DC signal of zero. Further, since the AC signal generated by waveform generator 186 is amplified by transformer circuit 184, waveform generator 186 may generate a low voltage AC signal.

For the preferred dual energy baggage scanner shown in FIGS. 1–3, as seen in FIG. 5, in order to further enhance the disparity between the energy levels of high and low energy beams passing through the baggage being scanned, the waveform generator 186 preferably includes a motor 260 for rotating a filter 262, a rotary shaft encoder 264, and a digital-to-analog converter 268. Filter 262 is a preferably flat disk that is disposed proximal to X-ray tube 128 for rotation within the beam generated by X-ray tube 128. Rotary shaft encoder 264 senses the angular position of filter 262 and generates a digital signal representative thereof, and applies this digital signal to digital-to-analog converter 268. The latter generates an analog signal representative of the digital signal generated by encoder 264 and applies the analog signal to amplifier 230 of power supply 200.

In the illustrated embodiment, filter 262 is a flat metal disk that is divided up into six equally sized "pie shaped" segments, although the number of segments can vary. Three of the segments 270 are formed from relatively thick sheets 128 of dense material (e.g., 0.6 mm of copper) that are sufficiently thick so as to absorb a portion of the low energy photons generated by X-ray tube 128 and are sufficiently thin so as to transmit substantially all of the high energy photons generated by tube 128. The three remaining segments 272 are formed from relatively thin sheets of light material (e.g., 0.1 mm of aluminum) and are sufficiently thinner than segments 270 so that segments 272 transmit a higher percentage of the low energy photons generated by tube 128. Segments 270 and 272 are alternately disposed so that each of the thick segments 270 is adjacent two of the thinner segments 272, and vice versa.

In operation, filter 262 rotates under the control of motor 260, and analog-to-digital converter 268 generates a periodically varying analog signal representative of the angular orientation of filter 262, and specifically indicating whether a segment 270 or a segment 272 is disposed in the beam 124. In the illustrated embodiment, converter 268 preferably generates a sinusoidal signal characterized by frequency $f_1$, where f is equal to three times the rotational frequency of filter 262. As stated above, the rate or frequency $f_1$ of the signal generated by converter 268 and applied to amplifier 230 controls the periodic rate at which the X-ray beam changes between high and low energy levels. Since the signal generated by converter 268 is synchronized with the rotation of filter 262, waveform generator 186 insures that the periodic rate of change of the X-ray beam between the two energy levels is synchronized with the rotation of filter 262.

In the illustrated embodiment, filter 262 preferably rotates 120° for every oscillation of the X-ray beam, and the initial position of filter 262 is adjusted so that one of the thicker sections 270 is disposed in the beam between the tube 128 and the baggage 112 (shown in FIG. 1) when tube 128 generates the high energy beam (i.e., when the voltage level between node A and system ground equals $V_1$), and one of the thinner sections 272 is disposed in the beam when tube 128 generates the low energy beam (i.e., when the voltage level between node A and system ground equals $V_2$). So filter 262 removes a portion of the low energy photons from the high energy beam and filter 262 removes few if any of the low energy photons from the low energy beam. So filter 262 acts to increase the disparity between the energy levels of the high and low energy beams generated by tube 128.

In the preferred embodiment, the rotation of filter 262 (and therefore the oscillation of the X-ray beam) is synchronized to the rotation of rotating disk 124 of the baggage scanner (shown in FIGS. 1–3), so that the X-ray beam periodically changes between the high and low energy levels and back to the high energy level (one cycle or period of the waveform) N times for every 360° rotation of disk 124, where N is an integer. In one preferred embodiment N is equal to 600, although this number can clearly vary. It will be appreciated that N low energy projections and N high energy projections will be thereby provided for each 360° rotation of disk 124. Synchronization of rotating disk 124 and filter 262 may be accomplished by well known means using what is commonly referred to as the "graticule" of a CT scanner to control the operation of a motor controller 280, which in turn controls the speed of motor 260. One such detection system, generally indicated at 282 in FIG. 5, is shown and described in U.S. Pat. No. 5,432,339, filed in the names of Bernard M. Gordon, Douglas Abraham, David Winston and Paul Wagoner, entitled Apparatus for and Method of Measuring Geometric, Positional and Kinematic Parameters of a Rotating Device Having a Plurality of Interval Markers, issued Jul. 11, 1995, and assigned to the present assignee. Since rotating disk 124 is a relatively large heavy device, it is difficult to insure that the rotational frequency of disk 124 always remains constant. Synchronizing the periodic rate of change $f_1$ of the X-ray beam to the rotation of disk 124 insures that the X-ray beam will periodically vary between the two energy levels the same number of times for every 360° rotation of platform 124. This insures that the same number of high and low energy projections will be generated for every 360° rotation of platform 124, even if the rotational frequency of platform 124 changes slowly during a scan. Since the rotational frequency of platform 124 is generally not constant and varies within a relatively small range, the rate of change $f_1$ of beam 134 is also not constant and also varies within a correspondingly small range. It should also be appreciated that the output of sensor 282 can also be used to control the linear speed of the baggage 112 through the scanner, for example by providing an input to a motor controller (not shown) which controls the motor driven conveyor system so that the linear speed of the conveyor system is both synchronized, and can be maximized to the rotational speed of the disk 124.

Waveform generator 186 therefore preferably performs several functions: waveform 186 (1) controls the periodic rate of change $f_1$ between the high and low energy levels of X-ray beam 132; (2) synchronizes this rate of change of the beam between the high and low energy states with the rotation of disk 124; and (3) synchronizes the periodic rate of change of beam 132 between the high and low energy states with the rotation of filter 262. Synchronizing the periodic rate of change of beam 132 with the rotation of disk 124 insures that the same number of high and low energy projections are generated for every 360° rotation of disk 124. While those skilled in the art will appreciate that it is desirable to generate the same number of high and low energy projections for every 360° rotation of platform 124, in other embodiments of the invention waveform generator 186 may not need to synchronize the periodic rate of change of beam 132 and the rotation of disk 124. Power supply 200 and X-ray tube 128 cooperate to generate a dual energy X-ray beam that periodically changes between two energy levels, and rotating filter 262 operates to increase the disparity between the energy levels of the beam that is incident on the baggage 112. However, in other embodiments of the invention, rotating filter 262 may be eliminated. In still other embodiments, other configurations of filter 262 (e.g., more or less than six segments) may be used e.g. to increase or decrease the number of high and low energy projections with each revolution of the disk.

Figure 8:
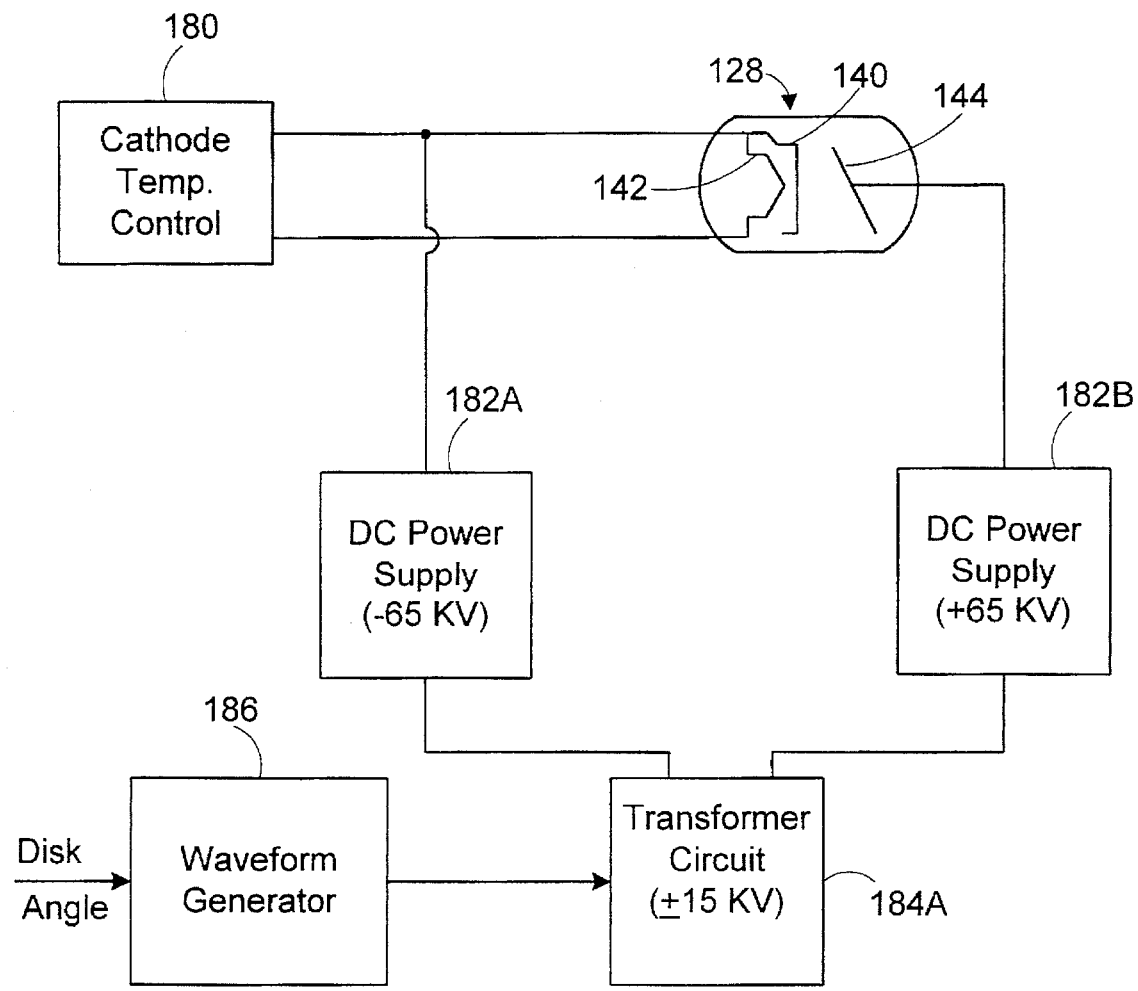
FIG. 8 shows a block diagram of a third preferred embodiment of the power supply and X-ray tube of the assembly shown in FIG. 1, designed according to the present invention.
Figure 9:
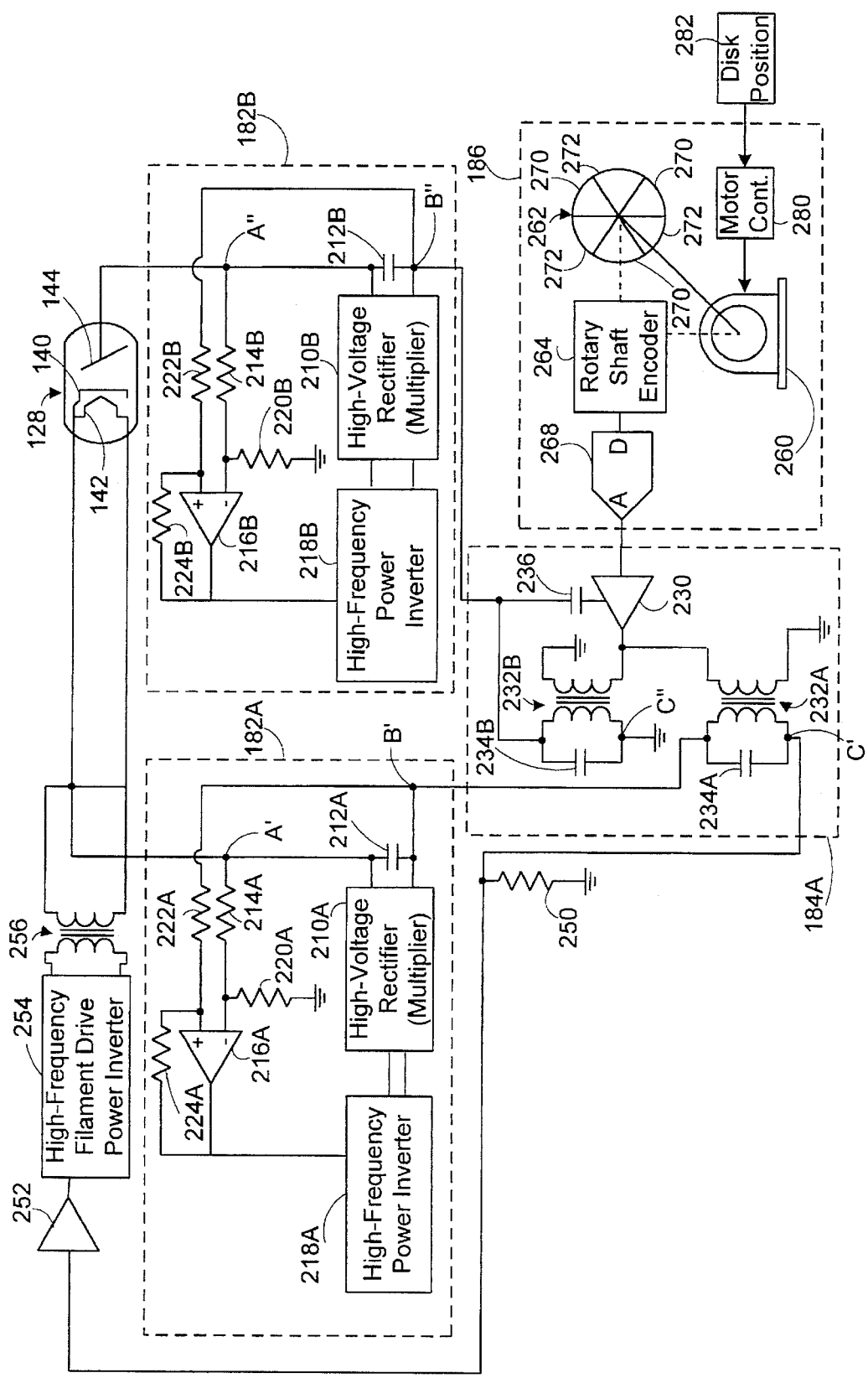
FIG. 9 shows a partial block and partial schematic diagram of a detailed illustration of the FIG. 8 embodiments.

An alternative and preferred embodiment to those shown in FIGS. 4 and 5 is shown in FIGS. 8 and 9. In FIG. 8 two stable, high voltage DC power supplies 182A and 182B are used to apply two high DC voltages to the respective cathode 142 and anode 144 of tube 128, and transformer circuit 184A couples the waveform generator 186 to the DC power supplies 182A and 182B so that an AC switching voltage is provided between each of the DC power supplies and system ground. In the example of the preferred embodiment the DC supplies 182A and 182B would provide respectively a −65 kV on the cathode 142 and a +65kV on the anode 144 so that the total DC bias voltage $V_3$ across the cathode and anode is −130 kV. In this embodiment the transformer circuit need only provide a modulating voltage of −15 kV and +15 kV to each of the cathode and anode to achieve the desired $V_1$ (−160 kV) and $V_2$ (−100 kV) voltages across the cathode and anode for providing the high and low energy beams respectively.

A more detailed illustration of one preferred implementation of the FIG. 8 embodiment is shown in FIG. 9. In FIG. 9, the cathode temperature control system 180 and waveform generator 186 are functionally identical to the corresponding parts in FIG. 5. The high DC voltage supplies 182A and 182B are identical to supply 182 shown in FIG. 5, except that each is designed to provide a stable DC voltage of −65 kV and +65 kV across the respective capacitors 212A and 212B, between nodes A' and B' and between A" and B" nodes, respectively. Accordingly, the connections to the inverting and non-inverting outputs of feedback amplifier 216B are reversed from that shown for feedback amplifier 216A, because of the reverse polarity of the DC voltage.

The transformer circuit 184A is also preferably modified as shown. More specifically, two transformers 234A and 234B are provided, one for providing a modulating voltage to the cathode 142, the other to the anode 144. The output of amplifier 230 is applied to and drives both primary windings of transformers 234A and 234B. The two separate secondary windings of transformers 234A and 234B are connected to the capacitors 234A and 234B to provide two separate LC circuits, each tuned to the periodic rate of change $f_1$. In the case where a voltage modulating between −160 kV and −100kV is required to be applied across the cathode 142 and anode 144, an AC modulating signal varying between +15 kV switching voltage is required across the two nodes B' and C' and the two nodes B" and C". If the output of amplifier 230 is +1 kV, the ratio of turns between the secondary and primary windings of each of the transformers 232A and 232B need only be 15:1 to provide the appropriate voltage multiplication. Further, the primary winding of transformer 232B is opposite to the primary winding of transformer 232A so that the two AC signals are 180° out of phase. It will be appreciated that the DC supplies 182A and 182B provide the stable −130 kV bias between the cathode 142 and anode 144 of tube 140, while the two AC signals generated between nodes B' and C' and between B" and C" provide the modulating voltage of ±30 kV. As with the embodiment shown in FIG. 5, the relative positions of transformer circuit 184A and DC power supplies 182A, 182B could of course be reversed.

The dual energy power supply of the present invention as shown by the embodiments of FIGS. 5, 7 and 9 provides distinct advantages. The transformer circuits 184 and 184A provide voltage outputs at a lower power level from that of the total power required. Generally, it is easier to modulate lower power levels. Secondly, each transformer circuit is attached at or near ground making it simpler to implement. The transformers 232, 232A and 232B provide a device for isolating the power levels delivered to the X-ray tube from the remaining portions of the device including the waveform generator. The transformer also provides a much better time response to the periodically varying signal than would the high voltage rectifiers 210, 210A, 210B of the high voltage DC power supplies. The transformer further allows the supply to generate the modulated voltages in an efficient manner while consuming a relatively small amount of power.

The transformer 232, 232A, 232B further provides the means for multiplying the output of amplifier 230, making it easy to design the amplifier 230 as a low voltage power amplifier, with for example conventional FETs and avoiding the need for power tubes typically used in high voltage power amplifiers.

Figure 10:
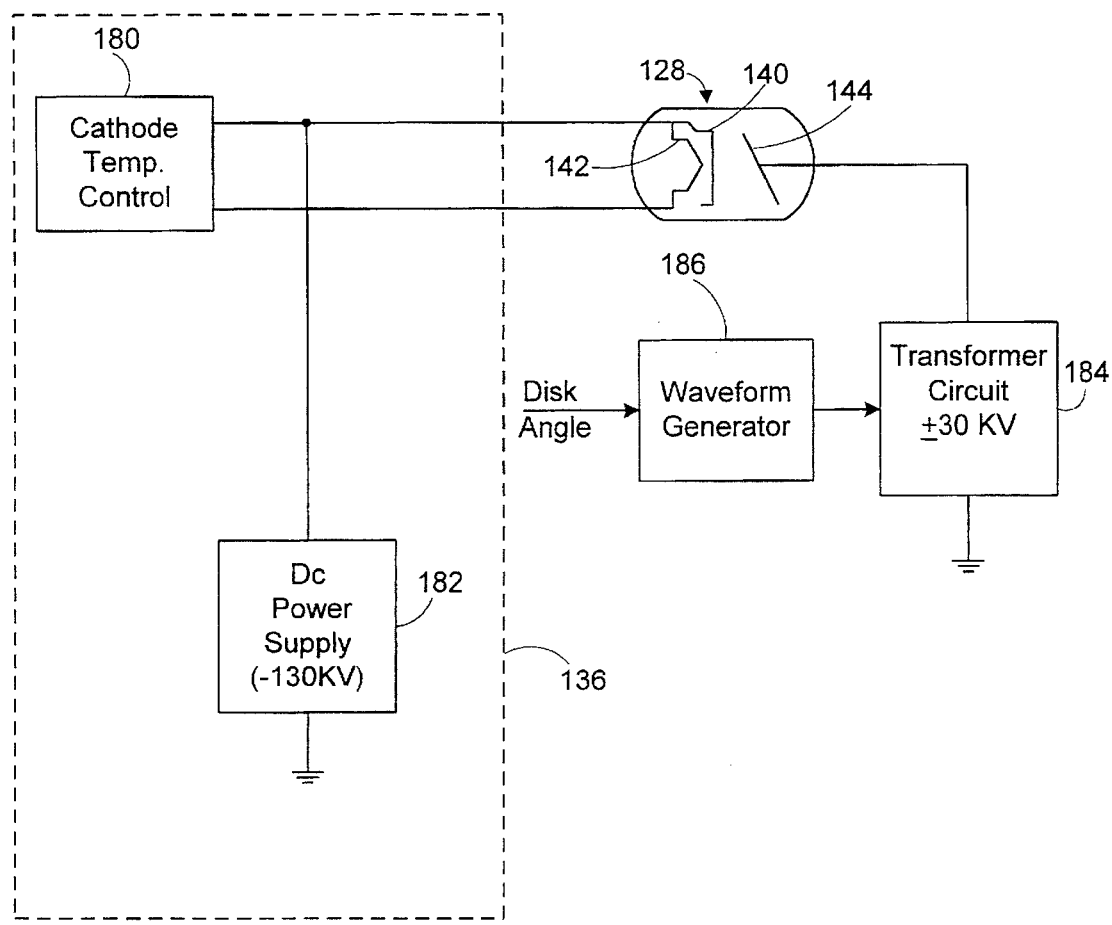
FIG. 10 shows a block diagram of a fourth preferred embodiment of the power supply and X-ray tube of the assembly shown in FIG. 1, designed according to the present invention.

Another alternative and preferred embodiment to those shown in FIGS. 4–9 is shown in FIG. 10. In this embodiment the stable, high voltage DC power supply 182 is connected to the cathode 142 of tube 128 as previously described so as to apply a high DC voltage to the cathode. However, the transformer circuit 184 is connected between the anode and system ground so that an AC switching voltage is provided to the anode.

The transformer circuit 184 couples the waveform generator 186 to the anode so that an AC switching voltage is provided between the anode and system ground. In the example of the preferred embodiment, the DC supply 182 would provide a −130 kV on the cathode 142, while the AC switching voltage modulates between +30 kV and −30 kV. This results in the desired first and second voltage levels of −100 kV and −160 kV, respectively.

The invention has been described in connection with a third generation type CT scanner, although those skilled in the art will appreciate that the invention may also be used with other types of X-ray equipment including for example fourth generation CT scanners. Further, while the scanner has been described as useful for scanning luggage, the system can be used for scanning other objects in large numbers such as packages or mail.

The improved power supply is thus provided for generating a periodic changing high voltage signal that changes between two high voltage levels at a relatively high changing rate and is particularly useful in driving an x-ray source at two different intensity levels at the changing rate. The improved high voltage power supply is particularly useful with a CT scanner for generating a dual energy X-ray beam, and can be used to provide an improved baggage scanner. The high voltage power supply provides a high voltage output which varies between two high voltage levels at a periodically varying, relatively fast rate with little or no power loss. The baggage scanner includes components for synchronizing the period of the dual energy X-ray beam with rotation of a rotating platform such as a rotating gantry disk. The scanner includes components for transporting items such as baggage through the CT scanner.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A power supply for use in alternately powering a X-ray tube having a cathode and anode at high and low voltage levels at a predetermined rate so that the tube generates a dual energy X-ray beam, the power supply comprising:
   at least one high DC voltage supply for providing a stable, high DC voltage to the X-ray tube;
   means, including at least one waveform generator, for providing a periodic time varying waveform; and
   coupling means, including a transformer, for coupling the waveform generator to said DC voltage supply so that the total voltage across the cathode and anode of the tube is periodically changed between the high and low voltage levels at the predetermined rate in response to the periodic time varying waveform provided by the waveform generator.

2. A power supply according to claim 1, wherein said waveform generator is coupled to the high DC voltage supply through said transformer so that the transformer provides DC isolation between the waveform generator and the DC voltage supply.

3. A power supply according to claim 2, wherein the coupling means provides a periodic time varying voltage across at least one output of the transformer between the cathode of said tube and the stable, high DC voltage output of said high DC voltage supply in response to the periodic time varying waveform provided by the waveform generator, and said high DC voltage supply provides said stable, high DC voltage between the transformer and system ground.

4. A power supply according to claim 2, wherein the coupling means provides a periodic time varying voltage across at least one output of the transformer between the anode of said tube and system ground in response to the periodic time varying waveform provided by the waveform generator, and said high DC voltage supply provides said stable, high DC voltage between the cathode of said tube and system ground.

5. A power supply according to claim 2, wherein said high DC voltage supply provides said stable, high DC voltage between the cathode of said tube and the transformer, and the coupling means provides a periodic time varying voltage across at least one output of the transformer between the high DC voltage and system ground in response to the periodic time varying waveform provided by the waveform generator.

6. A power supply according to claim 2, wherein said coupling means further includes a low voltage power amplifier providing a voltage output signal periodically varying at the predetermined rate in response to the periodic, time varying waveform provided by the waveform generator, and said transformer includes means for multiplying the amplitude of the voltage output signal of the power amplifier.

7. A power supply according to claim 6, wherein the transformer further includes at least one primary winding having a first predetermined number of turns and at least one secondary winding having a second predetermined number of turns, and the means for multiplying the amplitude of the voltage includes the ratio of the number of secondary turns to the number of primary turns.

8. A power supply according to claim 2, wherein the transformer includes a secondary winding coupled to a capacitor so as to provide an LC circuit tuned at a frequency determined by the predetermined rate.

9. A power supply according to claim 1, wherein the waveform generator includes a signal generating means for generating a periodic time varying signal at a periodic rate as a function of the predetermined rate.

10. A power supply according to claim 1, wherein the periodic rate of the periodic time varying waveform is a function of the angular position of a rotating object.

11. A power supply according to claim 10, wherein the X-ray tube generates an alternately changing high and low energy X-ray beam in response to the high and low voltage levels provided to the tube by said power supply, and the rotating object is a rotating filter positioned in the beam.

12. A power supply according to claim 11, wherein the filter has at least two segments of greater and lesser X-ray absorption characteristics, wherein the segments are alternately rotated in the beam, said means for providing a periodic time varying waveform further including means for synchronizing the rotation of said filter so that the segment of greater absorption is positioned in the beam when the X-ray tube is powered by the high voltage level, and the segment of lesser absorption is positioned in the beam when the X-ray tube is powered by the low voltage level.

13. A power supply according to claim 1, further including means for controlling the temperature of the cathode of said X-ray tube.

14. A power supply according to claim 1, further including a second high DC voltage supply, and said coupling means further includes two transformers, wherein one of said DC voltage supplies and one of said transformers are connected in series with one another and to said cathode, and the other of said DC voltage supplies and the other of said transformers are connected in series with one another and to said anode.

15. A power supply according to claim 14, wherein the transformers each have a primary winding coupled to said waveform generator.

16. In a CT system including an X-ray tube having a cathode and anode, a detector system for detecting X-rays emitted from said tube, means for rotating at least the tube about a rotation axis, and a power supply for use in alternately powering the X-ray tube at high and low voltage levels at a predetermined rate so that the tube generates a dual energy X-ray beam, the power supply comprising:
   at least one high DC voltage supply for providing a stable, high DC voltage to the X-ray tube;
   means, including at least one waveform generator, for providing a periodic time varying waveform; and
   coupling means, including a transformer, for coupling the waveform generator to said DC voltage supply so that the total voltage across the cathode and anode of the tube is periodically changed between the high and low voltage levels at the predetermined rate in response to the periodic time varying waveform provided by the waveform generator.

17. A system according to claim 16, wherein said waveform generator is coupled to the high DC voltage supply through said transformer so that the transformer provides DC isolation between the waveform generator and the DC voltage supply.

18. A power supply according to claim 17, wherein the coupling means provides a periodic time varying voltage across at least one output of the transformer between the cathode of said tube and the stable, high DC voltage output of said high DC voltage supply in response to the periodic time varying waveform provided by the waveform generator, and said high DC voltage supply provides said stable, high DC voltage between the transformer and system ground.

19. A power supply according to claim 17, wherein the coupling means provides a periodic time varying voltage across at least one output of the transformer between the anode of said tube and system ground in response to the periodic time varying waveform provided by the waveform generator, and said high DC voltage supply provides said stable, high DC voltage between the cathode of said tube and system ground.

20. A system according to claim 17, wherein said high DC voltage supply provides said stable, high DC voltage between the cathode of said tube and the transformer, and the coupling means provides the periodic time varying voltage across at least one output of the transformer between the high DC voltage and system ground in response to the periodic time varying waveform provided by the waveform generator.

21. A system according to claim 17, wherein said coupling means further includes a low voltage power amplifier providing a voltage output signal periodically varying at the predetermined rate in response to the periodic, time varying waveform provided by the waveform generator, and said transformer includes means for multiplying the amplitude of the voltage output signal of the power amplifier.

22. A system according to claim 21, wherein the transformer further includes at least one primary winding having a first predetermined number of turns and at least one secondary winding having a second predetermined number of turns, and the means for multiplying the amplitude of the voltage includes the ratio of the number of secondary turns to the number of primary turns.

23. A system according to claim 17, wherein the transformer includes a secondary winding coupled to a capacitor so as to provide an LC circuit tuned at a frequency determined by the predetermined rate.

24. A system according to claim 16, wherein the waveform generator includes a signal generating means for generating a periodic time varying signal at a periodic rate as a function of the predetermined rate.

25. A system according to claim 16, wherein the periodic rate of the periodic time varying signal is a function of the angular position of a rotating object.

26. A system according to claim 25, wherein the rotating object is the means for rotating at least the tube about the rotation axis.

27. A system according to claim 25, wherein the X-ray tube generates an alternately changing high and low energy X-ray beam in response to the high and low levels of voltage provided to the tube by said power supply, and the rotating object is a rotating filter positioned in the beam.

28. A system according to claim 27, wherein the filter has at least two segments of greater and lesser X-ray absorption characteristics, wherein the segments are alternately rotated in the beam, said waveform generator further including means for synchronizing the rotation of said filter so that the segment of greater absorption is positioned in the beam when the X-ray tube is powered by the high voltage level, and the segment of lesser absorption is positioned in the beam when the X-ray tube is powered by the low voltage.

29. A system according to claim 27, wherein the angular position of the rotating filter is a function of the angular position of the means for rotating at least the tube about the rotation axis.

30. A system according to claim 16, further including means for controlling the temperature of the cathode of said X-ray tube.

31. A system according to claim 16, wherein the power supply further includes a second high DC voltage supply, and said coupling means further includes two transformers, wherein one of said DC voltage supplies and one of said transformers are connected in series with one another and to said cathode, and the other of said DC voltage supplies and the other of said transformers are connected in series with one another and to said anode.

32. A system according to claim 31, wherein the transformers each have a primary winding coupled to said waveform generator.

33. A scanning system for scanning objects comprising a CT scanner having an X-ray tube having a cathode and anode, a detector system for detecting X-rays emitted from said tube, a conveyance system for successively moving said objects through the scanner, means for rotating at least the tube about a rotation axis around the objects as they are moved through the scanner, and a power supply for use in alternately powering the X-ray tube at high and low voltage levels at a predetermined rate so that the tube generates a dual energy X-ray beam, the power supply comprising:

at least one high DC voltage supply for providing a stable, high DC voltage to the X-ray tube;

means, including at least one waveform generator, for providing a periodic time varying waveform; and coupling means, including a transformer, for coupling the waveform generator to said DC voltage supply so that the total voltage across the cathode and anode of the tube is periodically changed between the high and low voltage levels at the predetermined rate in response to the periodic time varying waveform provided by the waveform generator.

34. A system according to claim 33, wherein said waveform generator is coupled to the high DC voltage supply through said transformer so that the transformer provides DC isolation between the waveform generator and the DC voltage supply.

35. A power supply according to claim 34, wherein the coupling means provides a periodic time varying voltage across at least one output of the transformer between the cathode of said tube and the stable, high DC voltage output of said high DC voltage supply in response to the periodic time varying waveform provided by the waveform generator, and said high DC voltage supply provides said stable, high DC voltage between the transformer and system ground.

36. A power supply according to claim 34, wherein the coupling means provides a periodic time varying voltage across at least one output of the transformer between the anode of said tube and system ground in response to the periodic time varying waveform provided by the waveform generator, and said high DC voltage supply provides said stable, high DC voltage between the cathode of said tube and system ground.

37. A system according to claim 34, wherein said high DC voltage supply provides said stable, high DC voltage between the cathode of said tube and the transformer, and the coupling means provides a periodic time varying voltage across at least one output of the transformer between the high DC voltage and system ground in response to the periodic time varying waveform generated by said waveform generator.

38. A system according to claim 34, wherein said coupling means further includes a low voltage power amplifier providing a voltage output signal periodically varying at the predetermined rate in response to the periodic, time varying waveform provided by the waveform generator, and said transformer includes means for multiplying the amplitude of the voltage output signal of the power amplifier.

39. A system according to claim 38, wherein the transformer further includes at least one primary winding having a first predetermined number of turns and at least one secondary winding having a second predetermined number of turns, and the means for multiplying the amplitude of the voltage includes the ratio of the number of secondary turns to the number of primary turns.

40. A system according to claim 34, wherein the transformer includes a secondary winding coupled to a capacitor so as to provide an LC circuit tuned at a frequency determined by the predetermined rate.

41. A system according to claim 33, wherein the waveform generator includes a signal generating means for generating a periodic time varying signal at a periodic rate as a function of the predetermined rate.

42. A system according to claim 33, wherein the periodic rate of the time periodic time varying signal is a function of the angular position of a rotating object.

43. A system according to claim 42, wherein the rotating object is the means for rotating at least the tube about the rotation axis.

44. A system according to claim 42, wherein the X-ray tube generates an alternately changing high and low energy X-ray beam in response to the high and low voltage levels provided to the tube by said power supply, and the rotating object is a rotating filter positioned in the beam.

45. A system according to claim 44, wherein the filter has at least two segments of greater and lesser X-ray absorption characteristics, wherein the segments are alternately rotated in the beam, said modulator further including means for synchronizing the rotation of said filter so that the segment of greater absorption is positioned in the beam when the X-ray tube is powered by the high voltage level, and the segment of lesser absorption is positioned in the beam when the X-ray tube is powered by the low voltage level.

46. A system according to claim 44, wherein the angular position of the rotating filter is a function of the angular position of the means for rotating at least the tube about the rotation axis.

47. A system according to claim 33, further including means for controlling the temperature of the cathode of said X-ray tube.

48. A system according to claim 33, wherein the power supply further includes a second high DC voltage supply, and said coupling means further includes two transformers, wherein one of said DC voltage supplies and one of said transformers are connected in series with one another and to said cathode, and the other of said DC voltage supplies and the other of said transformers are connected in series with one another and to said anode.

49. A system according to claim 48, wherein the transformers each have a primary winding coupled to said waveform generator.

* * * * *